United States Patent
Overaker et al.

(10) Patent No.: US 6,942,666 B2
(45) Date of Patent: Sep. 13, 2005

(54) EXPANDABLE CABLE ANCHOR

(75) Inventors: David W. Overaker, Annandale, NJ (US); Kevin L. Cooper, Flemington, NJ (US); David A. Dalessandro, Fanwood, NJ (US)

(73) Assignee: Ethicon, Inc., Somerville, NJ (US)

( * ) Notice: Subject to any disclaimer, the term of this patent is extended or adjusted under 35 U.S.C. 154(b) by 532 days.

(21) Appl. No.: 10/112,619

(22) Filed: Mar. 29, 2002

(65) Prior Publication Data

US 2003/0187444 A1 Oct. 2, 2003

(51) Int. Cl.[7] ............................................... A61B 17/84
(52) U.S. Cl. ................................... 606/72; 606/232
(58) Field of Search .................................. 606/72, 232

(56) References Cited

U.S. PATENT DOCUMENTS

| | | |
|---|---|---|
| 4,632,100 A | 12/1986 | Somers et al. |
| 4,870,957 A | 10/1989 | Goble et al. |
| 5,156,616 A | 10/1992 | Meadows et al. |
| 5,207,679 A | 5/1993 | Li |
| 5,217,486 A | 6/1993 | Rice et al. |
| 5,268,001 A | 12/1993 | Nicholson et al. |
| 5,395,372 A | 3/1995 | Holt et al. |
| 5,411,523 A | 5/1995 | Goble |
| 5,507,801 A | 4/1996 | Gisin et al. |
| 5,584,860 A | 12/1996 | Goble et al. |
| 5,662,658 A | 9/1997 | Wenstrom, Jr. |
| 5,725,529 A | 3/1998 | Nicholson et al. |
| 5,814,072 A | 9/1998 | Bonutti |
| 5,868,789 A | 2/1999 | Huebner |
| 5,935,129 A * | 8/1999 | McDevitt et al. ............. 606/72 |
| 5,948,002 A | 9/1999 | Bonutti |
| 5,968,044 A | 10/1999 | Nicholson et al. |
| 5,993,463 A | 11/1999 | Truwit |
| 6,033,430 A | 3/2000 | Bonutti |
| 6,136,001 A | 10/2000 | Michelson |
| 6,136,032 A | 10/2000 | Viladot Perice et al. |
| 6,312,448 B1 | 11/2001 | Bonutti |
| 6,554,852 B1 | 4/2003 | Oberlander |
| 2002/0143329 A1 | 10/2002 | Serhan et al. |

FOREIGN PATENT DOCUMENTS

| | | |
|---|---|---|
| WO | 9729693 | 8/1997 |
| WO | 0106909 | 2/2001 |

OTHER PUBLICATIONS

U.S. Appl. No. 10/609,336, "Surgical Anchor Inserter", filed Jun. 28, 2003.

\* cited by examiner

Primary Examiner—David O. Reip

(57) ABSTRACT

A bone anchoring device for securing suture or cable within a bone hole opening of a bone includes a radially expandable sheath, an expander member for expanding the sheath and a washer. The cable or suture is secured within the bone hole opening such that an end tip thereof is knotted or secured to the washer to prevent separation therefrom. The cable or suture is not affected by the bearing load placed on the expander member during anchor deployment, and the bearing load acting on the cable member is transferred through the washer to the sheath, and not to the expander member.

24 Claims, 7 Drawing Sheets

EXPANDABLE CABLE ANCHOR

FIELD OF THE INVENTION

The present invention relates to bone anchoring devices, and, more specifically, to an expandable sheath for securing a cable within a hole opening in a bone.

BACKGROUND OF THE INVENTION

A wide variety of techniques are available to surgeons for securing sutures or cables within a hole opening in a bone. Screws, rivets, and other types of interference fitting anchors are commonly used.

One type of bone fastener includes an expandable member having an axial channel and an elongated insertion element insertable therein. When the insertion element is driven into the axial channel in the expandable member, an interference or interlocking fit secures the insertion element to the expander, thereby securing the suture within the bone hole opening. Load forces exerted on the suture act directly on the insertion element so that the security of the suture within the bone hole opening depends on the security of the engagement between the insertion element and the expandable member.

In the foregoing circumstances, what is needed is an expandable sheath in which the cable load (bearing force) acts directly on an expandable sheath that is expanded by an expander member for an interference fit within a hole opening in a bone. Such a device would provide the advantage that cable load (bearing force) acts directly on the expandable sheath so that the fastening strength of the anchor is independent of the axial security of engagement between the expander member and the expandable sheath. Such a bone anchoring device avoids the failure mode of expander separation from the expandable sheath under suture loading.

SUMMARY OF THE INVENTION

The problems and disadvantages of prior art devices described above are overcome by the present invention through the provision of a bone anchoring device which includes a radially expandable sheath, a washer and an expander member for expanding the sheath. The washer resides distal to the sheath and the expander member resides proximal to the sheath before deployment. The expander member and washer have axial passages to allow a cable member to pass through and beyond the distal side of the washer. The cable member is secured to the washer to prevent separation therefrom. In use, the bone anchor is placed into a bone hole opening, the cable member is held to prevent distal migration of the sheath, and the expander member is driven inwardly into the sheath to force it to expand radially to engage the walls of the bone hole opening of the bone. Once the anchor is fully deployed, the bearing load acting on the cable member acts through the washer directly to the sheath, which is radially compressed against the walls of the bone hole opening to resist proximal migration (i.e., movement out of the bone hole opening).

BRIEF DESCRIPTION OF THE DRAWINGS

Further objects, features and advantages of the present invention will become apparent upon consideration of the following detailed description of the exemplary embodiments considered in connection with the accompanying drawings, in which.

DETAILED DESCRIPTION OF THE EXEMPLARY EMBODIMENTS

Figure 1:
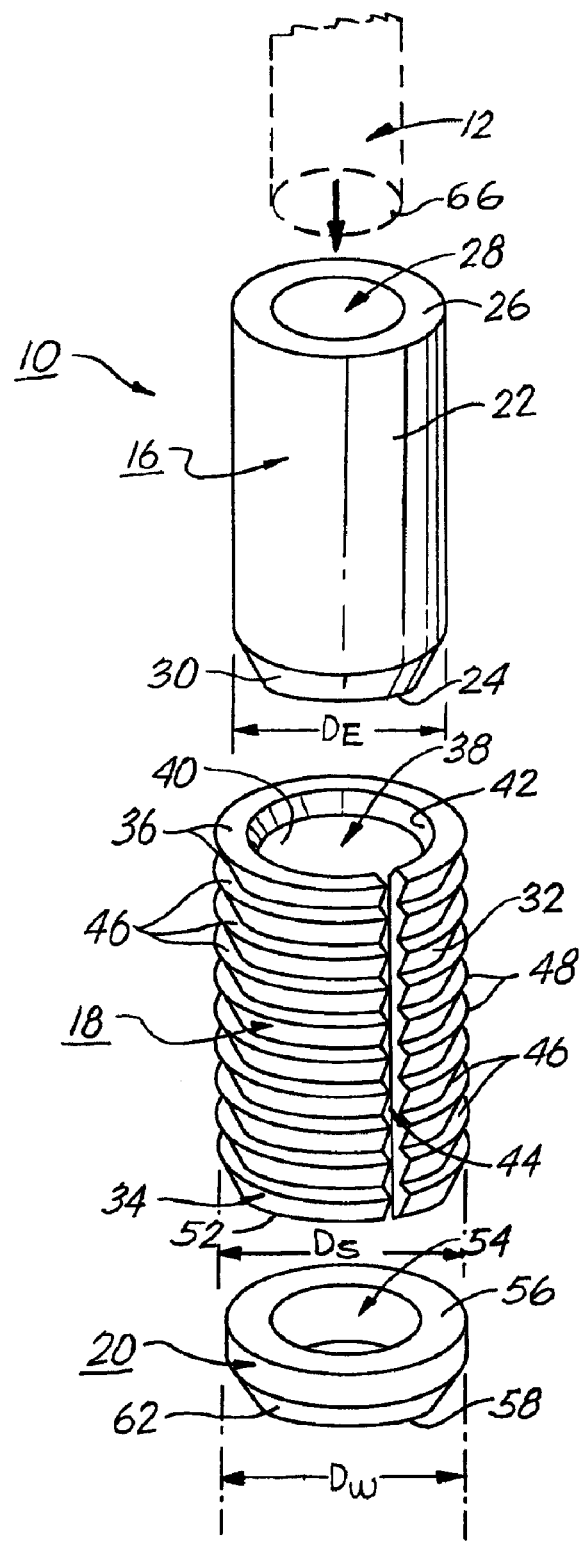
FIG. 1 is an exploded perspective view of a bone anchoring device constructed in accordance with a first exemplary embodiment of the present invention, a cable or suture being shown in phantom to facilitate consideration and discussion.

Referring to FIG. 1, there is shown a bone anchoring device 10 for use in surgical procedures in the securing of a cable member 12 to a bone of an effected patient. The cable member 12 as used herein refers to a long, generally cylindrical fibrous structure such as braided or woven rope or suture.

The bone anchoring device 10 includes an expander member 16, an expandable sheath 18 and a washer 20. The cable member 12 passes through the components 16, 18 and 20 and is knotted or attached to the washer 20. This results in a bone anchoring device 10 in which anchor failure due to separation of the expander member 16 from the expandable sheath 18 (being the loss of interference engagement with the surrounding bone) is avoided and/or prevented. A further advantage of the bone anchoring device 10 is that the mechanism of anchor deployment does not affect the position of the cable member 12 within the expandable sheath 18 (see FIGS. 2 and 3).

Figure 2:
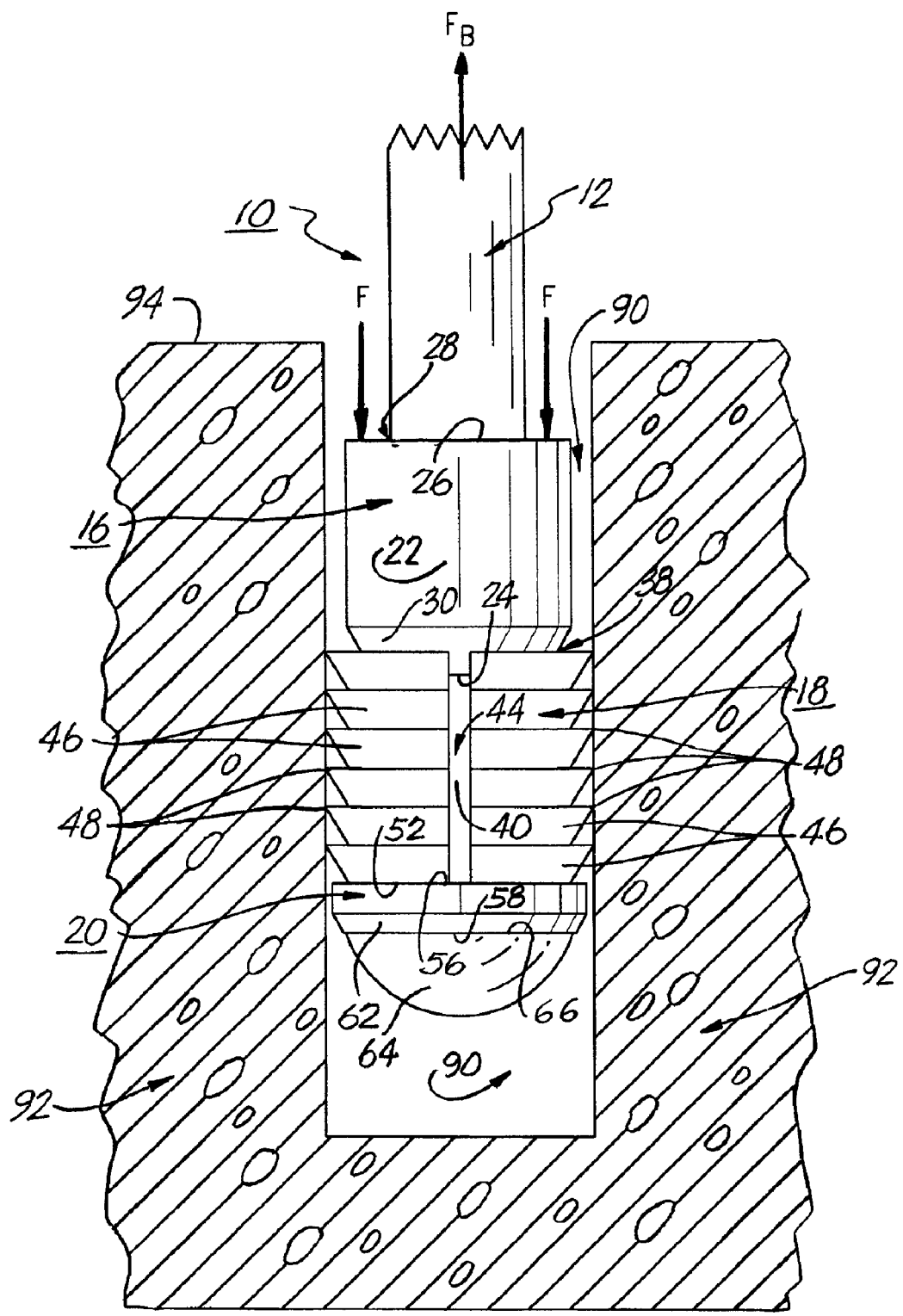
FIG. 2 is a side elevational view of the bone anchoring device of FIG. 1, the device being shown in an assembled configuration prior to deployment in a bone hole opening.
Figure 3:
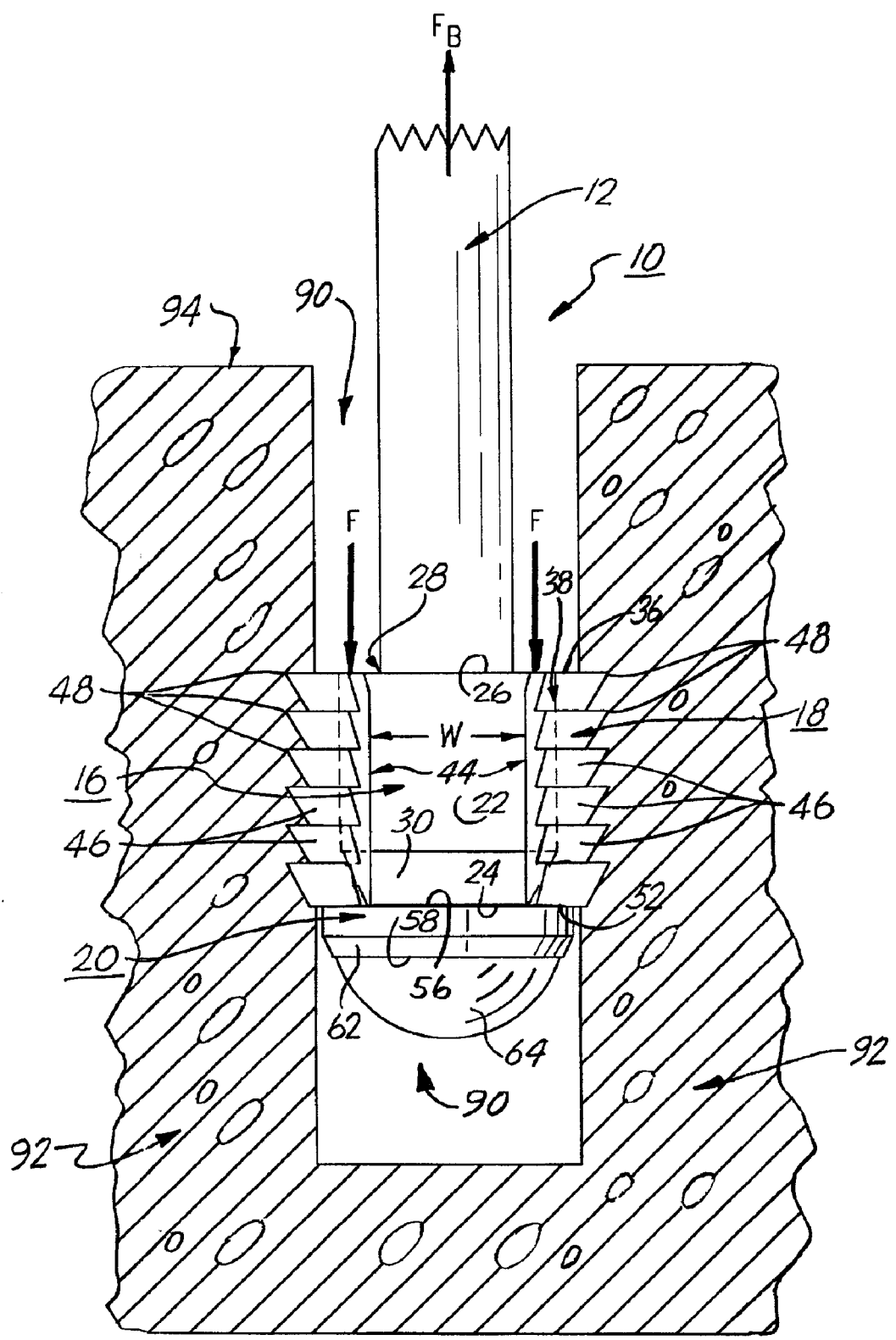
FIG. 3 is a side elevational view of the bone anchoring device of FIG. 2, the device being shown in a deployed state within the bone hole opening.

With reference to FIGS. 1–3, the expander member 16 is generally cylindrically-shaped and includes an outer wall surface 22, a distal surface end 24 and a proximal surface end 26. The expander member 16 further includes an axial channel 28 that passes entirely through the length of the expander member 16 (see FIG. 1), thereby imparting a tubular shape to the expander member 16. The expander member 16 also includes a chamfered or beveled edge 30 located at the distal surface end 24 of the expander member 16 (see FIG. 1). The chamfered edge 30 is used to serve as lead-in for the initial insertion of the expander member 16 into the expandable sheath 18 as shown in FIG. 2.

Referring still to FIGS. 1–3, the expandable sheath 18 is generally cylindrically-shaped and includes an outer wall surface 32, a distal end 34 and a proximal end 36. The expandable sheath 18 further includes an axial passageway 38 that passes entirely through the length of the expandable sheath 18 (see FIG. 1). The axial passageway 38 includes an inner wall surface 40. The expandable sheath 18 also includes a chamfered or beveled edge 42 located on the inner wall surface 40 at the proximal end 36 of sheath 18 (see FIG. 1). The chamfered edge 42 is used to serve as a receiving surface for the initial insertion of the chamfered edge 30 (at the distal end 24) of the expander member 16 into the expandable sheath 18 at the proximal end 36 as depicted in FIGS. 1 and 2. The diameter of the axial passageway 38 of sheath 18 is smaller than the outer diameter of expander member 16. The expandable sheath 18 also includes a longitudinally aligned slot 44 that passes through one side of the expandable sheath 18 (see FIG. 1). The slot 44 allows for the radial expansion of the expandable sheath 18 upon the full insertion of the expander member 16 within the sheath 18 as shown in FIG. 3 (to be fully described hereinafter). The outer wall surface 32 of sheath 18 includes a plurality of engagement ribs 46, each one having an engagement edge 48 for engaging the bone tissue within a bone hole opening in which the bone anchoring device 10 is deployed as depicted in FIG. 3. The ribs 46 are circumferentially aligned, as well as being transversely aligned relative to slot 44. Alternatively, the ribs 46 could have a helical configuration. Additionally, the distal end 34 includes a distal end wall surface 52 for interfacing with washer 20. The overall length of the expandable sheath 18 and the expander member 16 are equal in size.

Referring now to FIG. 1, the washer 20 has a generally cylindrical shape and includes an axial opening 54 therethrough, a proximal surface 56, a distal surface 58 and an outer diameter. The distal surface 58 includes a chamfered or beveled edge 62, which serves as a lead-in for the insertion of the washer 20 into the bone hole opening in which the bone anchoring device 10 is to be deployed (see FIG. 2). The proximal surface 56 of the washer 20 abuts and is in contact with the distal end wall surface 52 of expandable sheath 18, when in the assembled configuration (see FIGS. 2 and 3). The axial channel 28 of expander member 16, the axial passageway 38 of expandable sheath 18, and the axial opening 54 of washer 20 have diameters selected to allow the cable member 12 to pass therethrough such that a cable tip 64 of cable member 12 resides just beyond the distal surface 58 of washer 20. The outer diameter $D_w$ of washer 20 is preferably equal to the outermost diameter $D_s$ of sheath 18 and larger than the outermost diameter $D_E$ of expander member 16.

FIGS. 2 and 3 demonstrate the expansion of the bone anchoring device 10 for an interference fit in a bone hole opening within a patient. This expansion of the bone anchoring device 10 is achieved by the inwardly driving of the expander member 16 by a force F into the axial passageway 38 of the expandable sheath 18. The interference fit between the outer wall surface 22 of expander member 16 and the inner wall surface 40 of the axial passageway (of expandable sheath 18) forces the sheath 18 to expand radially to conform to the expander member 16. The sheath 18 expands radially due to the further separation of slot 44 with the full insertion of the expander member 16 within the axial passageway 38 of the expandable sheath 18. When the bone anchoring device 10 is fully deployed, as shown in FIG. 3, the proximal surface end 26 of expander member 16 is flush with the proximal (surface) end 36 of the expandable sheath 18 and the slot 44 has increased in width. The diameter of the axial passageway 38 of sheath 18 remains smaller than the outer diameter $D_w$ of washer 20 in order to prevent the proximal migration of washer 20 through the axial passageway 38 of sheath 18 (see FIG. 3).

FIGS. 2 and 3 show the initial and final configurations, respectively, of the bone anchoring device 10 when deployed in a bone hole opening 90 in order to anchor the cable member 12 to bone 92. A distal end 66 of cable member 12 passes through each of the axial openings 28, 38 and 54 of components 16, 18 and 20, respectively, wherein the cable tip 64 is formed from the distal end 66 of cable member 12. The tip 64 of cable member 12 resides just beyond the distal surface 58 of washer 20, and the outer diameter of the formed cable tip 64 is larger than the inner diameter of the axial opening 54 of washer 20. The cable tip 64 may be a knot, a section of the cable member 12 that has been heated and slightly melted such that a diameter increase is gained (a process known as "tipping"), or a weld section to the distal surface 58 of washer 20. Cable tip 64 may also be formed by molding material onto the cable member 12. The function of cable tip 64 is to prevent the cable member 12 from being removed from the axial opening 54 of washer 20.

FIG. 2 shows the initial deployment configuration of the bone anchoring device 10 which demonstrates the placement of the expander member 16, the expandable sheath 18, the washer 20 and the cable member 12 within the bone hole opening 90. The diameter of the bone hole opening 90 is equal to or only slightly larger than the outer diameter of washer 20. The bone anchoring device 10 is placed within the bone hole opening 90 such that the proximal surface end 26 of the expander member 16 is flush or below surface 94 of bone 92 (see FIG. 2). The chamfered edge 30 of the expander member 16 is in contact with the chamfered edge 42 of the expandable sheath 18 in the initial configuration (expander member 16 has not been deployed within sheath 18). When the sheath 18 is positioned at the appropriate depth, the cable member 12 is held sufficiently in order to prevent any distal migration of sheath 18 further into the bone opening as an inwardly acting force F is applied to the proximal surface end 26 of expander member 16. The expander member 16 is then forcibly driven into the axial passageway 38 of the expandable sheath 18 until full deployment is achieved (see FIG. 3).

With reference to FIG. 3, the bone anchoring device 10 is shown in its full deployment and final configuration. The expandable sheath 18 is shown expanded to a diameter to interfere with the diameter of the bone hole opening 90 allowing the engagement edges 48 of ribs 46 to engage and cut into the soft tissue of bone 92. FIG. 3 also shows the increasing of width W of the slot 44 when deployment of the expander member 16 within the sheath 18 is completed. The expansion of slot 44 allows uninhibited circumferential expansion of the expandable sheath 18 for accommodating the circumference of the expander member 16. The advantage of slot 44 is that it provides for the uniform radial expansion along the entire length of sheath 18 and thus, allows for very large radial and elastic expansion of sheath 18. The washer 20 allows the sheath 18 to expand completely without constraint at its distal end 34, while still maintaining the ability to transmit the force F from the cable member 12 to the sheath 18.

The main advantage of this mechanism of deployment with regard to the bone anchoring device 10 of the present invention is that the position of the expandable sheath 18 and the tip 64 of cable member 12 is fixed while the expander member 16 is driven inwardly (downward with respect to FIG. 3) by the force F in order to achieve fixation within the bone hole opening 90 of the bone 92. This deployment allows for the proper anchor placement of the bone anchoring device 10, while maintaining the desired tension of the cable member 12 during such deployment.

Once the bone anchoring device 10 is fully deployed in its final configuration as shown in FIG. 3, the bearing force (load) $F_B$ acting on the cable member 12 also acts upon the washer 20, such that the washer 20 is restricted from moving proximally (upwardly in the direction of the bearing force $F_B$) by contact with the adjacent sheath 18, wherein the sheath 18 is compressed against and fixed within the bone hole opening 90. Thus, the washer 20 serves to transmit the bearing force $F_B$ from the cable member 12 to the sheath 18 rather than solely to the expander member 16, such that the fixation strength of the bone anchoring device 10 to bone is independent of the strength of the axial engagement between the expander member 16 and the sheath 18.

Figure 4:
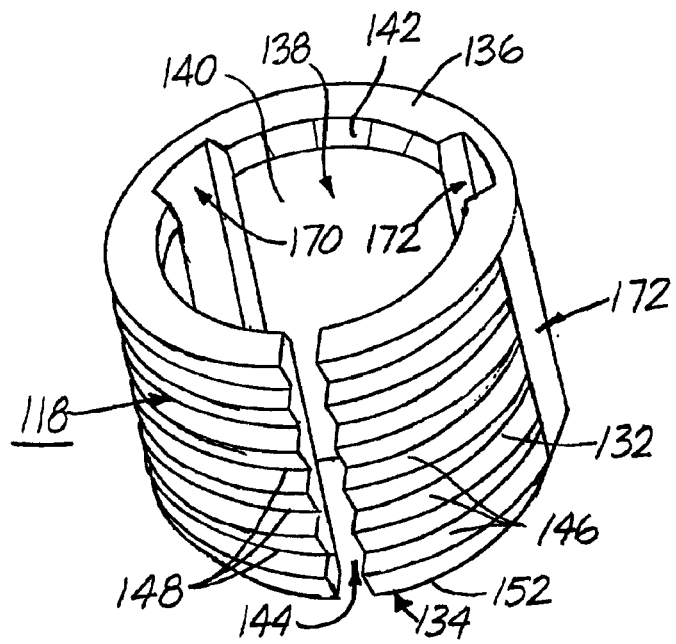
FIG. 4 is a perspective view of a sheath component constructed in accordance with a first alternate sheath design.

With reference to FIG. 4, a first alternate embodiment of the expandable sheath 18 is shown. Elements illustrated in FIG. 4 which correspond to the element described above with reference to FIGS. 1 and 3 have been designated by corresponding reference numbers increased by one hundred. The first alternate sheath embodiment of FIG. 4 is constructed and operates in the same manner as the expandable sheath 18 of bone anchoring device 10, unless it is otherwise stated.

As shown in FIG. 4, an expandable sheath 118 includes a pair of spaced-apart and longitudinally aligned outer wall hinges 170 and 172, each of which is integrally connected to the outer wall surface 132. More particularly, each of the outer wall hinges 170 and 172 is a circumferential (curved) segment of the outer wall surface 132 having a reduced thickness, as well as a reduced bending stiffness. The width and depth (thickness) of the outer wall hinges 170, 172 determines the bending flexibility of the hinges 170, 172 and therefore the overall radial flexibility of the sheath 118. The outer wall hinges 170, 172 provide the sheath 118 with greater radial flexibility when receiving the expander member 16 therein. While two hinges 170, 172 are shown, it should be understood that a single hinge could be employed or more than two hinges could be employed.

Figure 5:
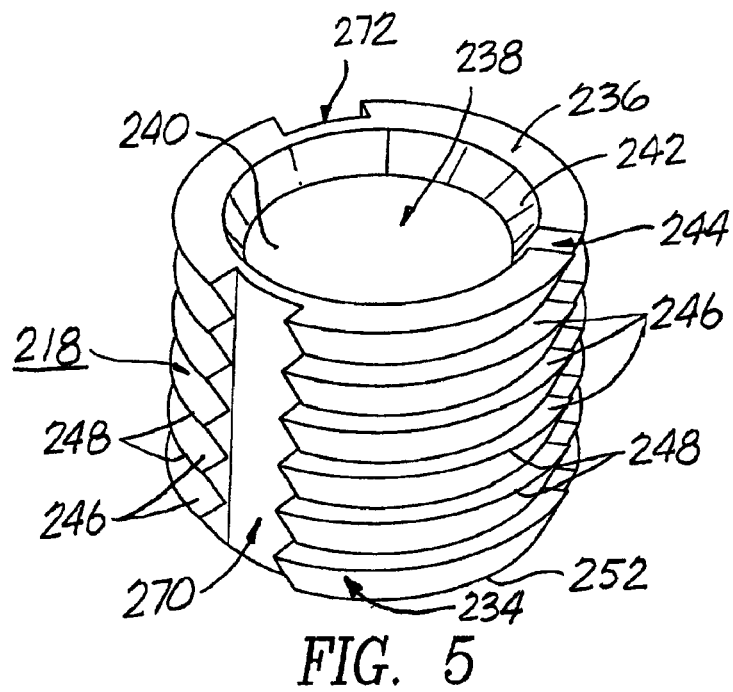
FIG. 5 is a perspective view of a sheath component constructed in accordance with a second alternate sheath design.

A second alternate embodiment of the expandable sheath 18 is illustrated in FIG. 5. Elements illustrated in FIG. 5 which correspond to the elements described above with reference to FIG. 4 have been designated by corresponding reference numbers increased by one hundred. The second alternate sheath embodiment of FIG. 5 is constructed and operates in the same manner as the sheath 118, unless it is otherwise stated.

With reference to FIG. 5, an expandable sheath 218 is exactly the same as the expandable sheath 118, except that the hinges 270 and 272 are located on the inner wall surface 280 (hence inner wall hinges 270, 272). The width and depth (thickness) of the inner wall hinges 270, 272 determines the bending flexibility of the hinges 270, 272 and therefore the overall radial flexibility of the sheath 218. While two hinges 270, 272 are shown, it should be understood that a single hinge could be employed or more than two hinges could be employed. Sheath 218 is preferred over sheath 118, because the engagement ribs 246 on the outer wall surface 232 of sheath 218 are not compromised when interacting with the surrounding bone tissue within the bone hole spacing.

Figure 6:
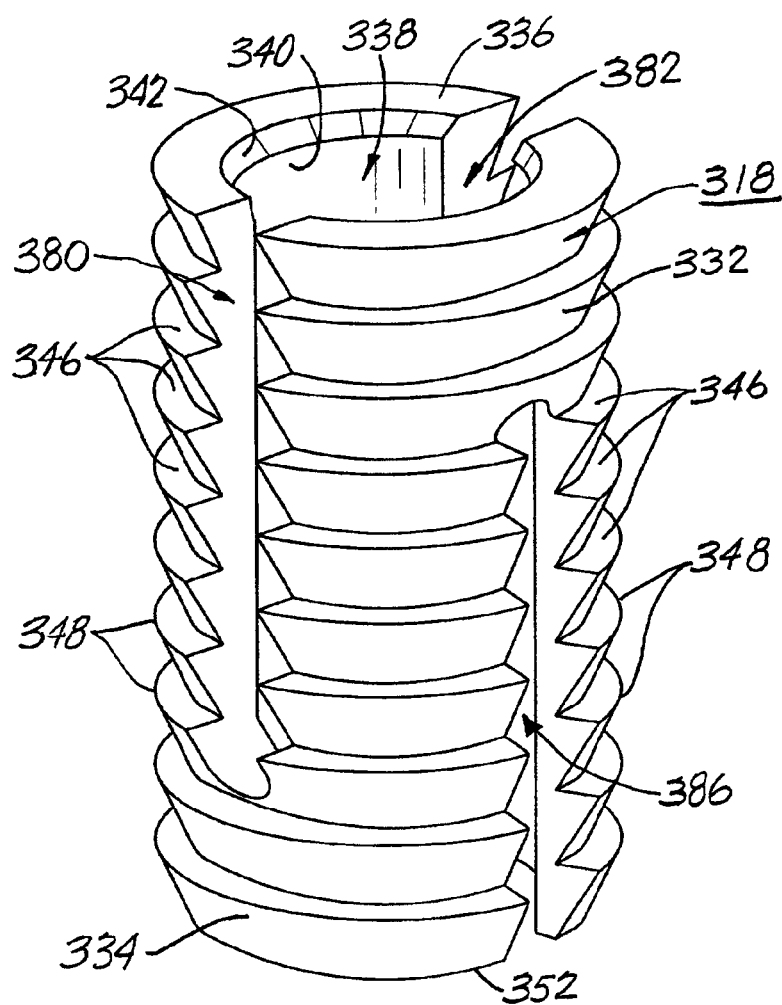
FIG. 6 is a perspective view of a sheath component constructed in accordance with a third alternate sheath design.

A third alternate embodiment of the expandable sheath 18 is illustrated in FIG. 6. Elements illustrated in FIG. 6 which correspond to the elements described above with reference to FIGS. 1 and 3 have been designated by corresponding reference numbers increased by three hundred. The third alternate sheath embodiment of FIG. 6 is constructed and operates in the same manner as the expandable sheath 18 of bone anchoring device 10, unless it is otherwise stated.

Figure 6A:
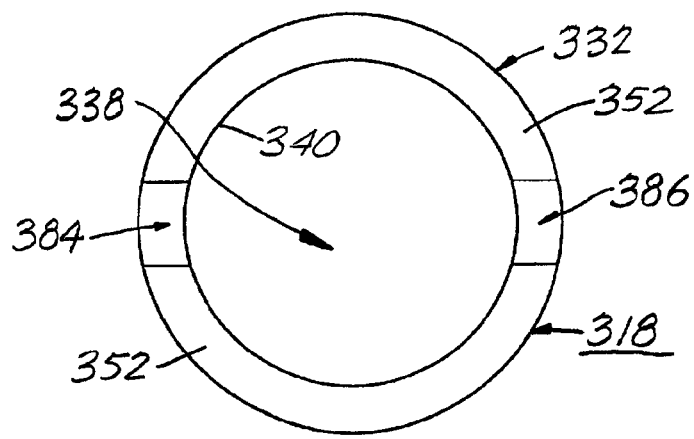
FIG. 6a is a bottom plan view of the sheath component of FIG. 6 showing a pair of opposed distal slot openings.

With reference to FIGS. 6 and 6a, an expandable sheath 318 includes a pair of spaced-apart and longitudinally aligned proximal slots 380, 382. The proximal slots 380, 382 extend downwardly through a substantial portion of the sheath 386 (but not entirely cut through). The expandable sheath 318 also includes a pair of spaced-apart and longitudinally aligned distal slots 384, 386. The distal slots 384, 386 extend upwardly through a substantial portion of the sheath 318 (but not entirely cut through). The distal slots 384, 386 are oriented on a plane orthogonal to the plane of orientation of the proximal slots 380, 382. These slots 380, 382, 384 and 386 provide bending flexibility to neighboring sections of sheath 318.

Figure 7:
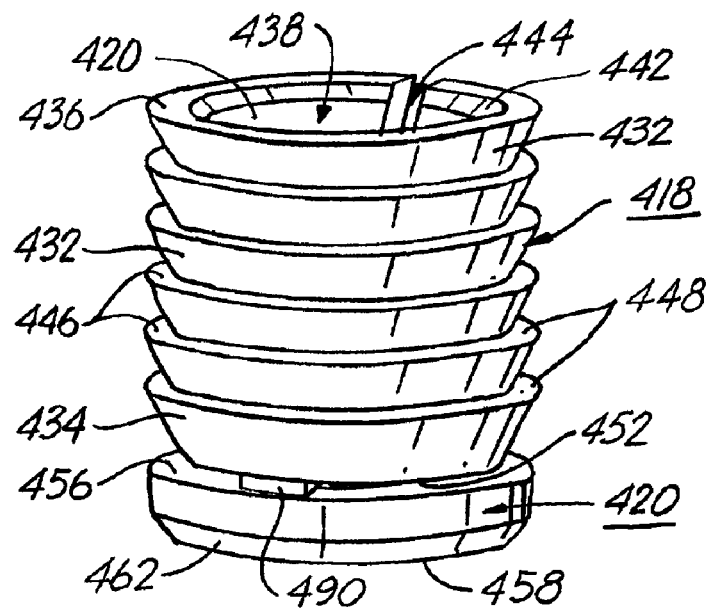
FIG. 7 is a perspective view of a sheath component constructed in accordance with a fourth alternate sheath design.
Figure 7A:
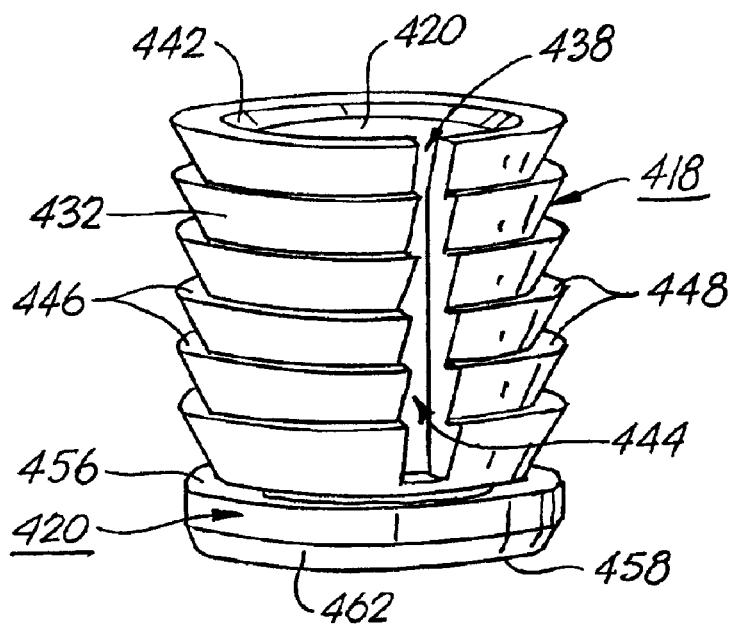
FIG. 7a is a perspective view of the sheath component of FIG. 7, the sheath having been rotated about its longitudinal axis to show a single slot opening therein.

With reference now to FIGS. 7 and 7a, a fourth alternate embodiment of the expandable sheath 18 is shown. Elements illustrated in FIGS. 7 and 7a which correspond to the elements described above with reference to FIGS. 1 to 3 have been designated by corresponding reference numbers increased by four hundred. The fourth alternate embodiment of FIG. 7 is constructed and operates in the same manner as the sheath 18 of bone anchoring device 10, unless it is otherwise stated.

As shown in FIGS. 7 and 7a, an expandable sheath 418 and a washer 420 are connected by a connecting tab 490. The tab 490 extends from the proximal end surface 456 of the washer 420 to the distal end surface 452 of the sheath 418. The tab 490 intersects the sheath 418 at the distal end 434 and is positioned 180 degrees from the position of slot 444. The tab 490 is positioned such that it has minimal effect on the expandability of the sheath 418. The advantage of this embodiment is the improved ease and efficiency of manufacturing the integrated sheath and washer versus manufacturing and handling the sheath and washer separately.

Figure 8:
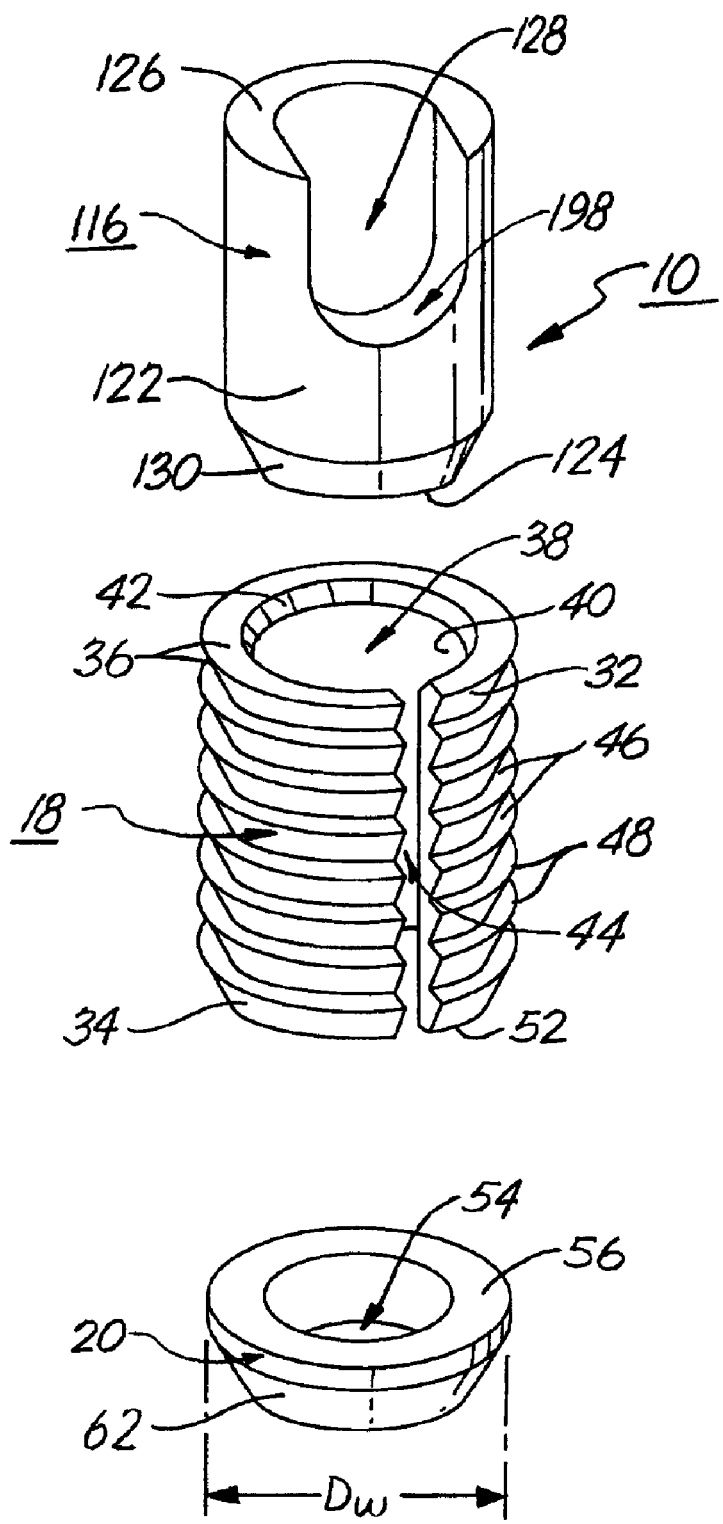
FIG. 8 is a perspective view of an expander component constructed in accordance with an alternate expander design.

An alternate embodiment of the expander member 16 is illustrated in FIG. 8. Elements illustrated in FIG. 8 which correspond to the elements described above with reference to FIG. 1 have been designated by corresponding reference numbers increased by one hundred. The alternate expander member of FIG. 8 is constructed and operates in the same manner as the expander member 16 of bone anchoring device 10, unless it is otherwise stated.

With reference to FIG. 8, the expander member 116 includes a U-shaped notch 198 formed in an outer wall 122. When the bone anchoring device 10 is deployed, the U-shaped notch 198 is aligned with the expansion slot 44 of sheath 18, such that the cable member 12 may pass through the U-shaped notch 198 and slot 44 in order to more easily access washer 20.

Bone anchoring device 10 of the present invention may be used to secure suture or cable within a hole opening in bone for a variety of uses. Uses include reattachment of ligaments or tendons to bond. Furthermore, cable member 12 of bone anchoring device 10 could be connected to a second bond anchoring device (not shown), which is secured within a second hole opening in bone. This arrangement could be used, for example, to hold a bone block between adjacent vertebrae in spinal fusion procedures.

Suitable materials from which the bone anchoring device 10 may be formed include biocompatible polymers such as aliphatic polyesters, polyorthoesters, polyanhydrides, polycarbonates, polyurethanes, polyamides and polyalkylene oxides. The present invention also can be formed from absorbable glasses or ceramics comprising calcium phosphates and other biocompatible metal oxides (i.e., CaO), metals, combinations of metals, autograft, allograft, or xenograft bone tissues.

In the preferred embodiment, the bone anchoring device 10 is formed from aliphatic polymer and copolymer polyesters and blends thereof. The aliphatic polyesters are typically synthesized in a ring opening polymerization. Suitable monomers include but are not limited to lactic acid, lactide (including L-, D-, meso and D,L mixtures), glycolic acid, glycolide, ε-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, α,alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof. These monomers generally are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization typically is carried out at a temperature range from about 80° C. to about 240° C., preferably from about 100° C. to about 220° C., until the desired molecular weight and viscosity are achieved.

In another embodiment of the present invention, the polymers and blends can be used as a therapeutic agent release matrix. Prior to forming the bone anchoring device 10, the polymer would be mixed with a therapeutic agent. The variety of different therapeutic agents that can be used in conjunction with the polymers of the present invention is vast. In general, therapeutic agents which may be administered via the pharmaceutical compositions of the invention include, without limitation: antiinfectives such as antibiotics and antiviral agents; chemotherapeutic agents (i.e. anticancer agents); anti-rejection agents; analgesics and analgesic combinations; anti-inflammatory agents; hormones such as steroids; growth factors, including bone morphogenic proteins (i.e. BMP's 1-7), bone morphogenic-like proteins (i.e. GFD-5, GFD-7 ana GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β I-III), vascular endothelial growth factor (VEGF); and other naturally derived or genetically engineered proteins, polysaccharides, glycoproteins, or lipoproteins.

Matrix materials for the present invention may be formulated by mixing one or more therapeutic agents with the polymer. Alternatively, a therapeutic agent could be coated on to the polymer, preferably with a pharmaceutically acceptable carrier. Any pharmaceutical carrier can be used that does not dissolve the polymer. The therapeutic agent may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

It should be understood that the embodiments described herein are merely exemplary and that a person skilled in the art may make many variations and modifications without departing from the spirit and scope of the present invention. All such variations and modifications are intended to be included within the scope of the invention as defined in the appended claims.

We claim:

1. A bone anchor, comprising a radially expandable sheath having a first passageway which extends axially through said sheath from a proximal end thereof to a distal end thereof; a washer having a second passageway which extends axially through said washer from a proximal end thereof to a distal end thereof, said proximal end of said washer being positionable in abutment with said distal end of said sheath such that said first and second passageways are substantially aligned, said sheath and said washer being sized and shaped such that no portion of said sheath extends into said second passageway of said washer when said sheath is in abutment with said washer; and expanding means for radially expanding said sheath without expanding said washer, said expanding means being insertable into said first passageway of said sheath from said proximal end thereof toward said distal end thereof.

2. A bone anchor according to claim 1, wherein said expanding means includes a tubular member having a third passageway extending from a proximal end of said tubular member to distal end thereof, said third passageway being arranged substantially coaxially relative to said first and second passageways, whereby a cable member can be passed through said first, second and third passageways and attached to said washer.

3. A bone anchor according to claim 2, wherein said sheath has an inner diameter which, prior to the radial expansion of said sheath, is determined by the size of said first passageway; and wherein said tubular member has an outer diameter which is greater than said inner diameter of said sheath prior to the radial expansion of said sheath.

4. A bone anchor according to claim 3, wherein said inner diameter of said sheath is increased in response to the insertion of said tubular member into said first passageway of said sheath.

5. A bone anchor according to claim 4, wherein said inner diameter of said sheath and said outer diameter of said tubular member are selected so as to create an interference fit between said sheath and said tubular member.

6. A bone anchor according to claim 5, wherein said sheath has a chamfered edge at said proximal end thereof; and wherein said tubular member has a beveled edge at said distal end thereof, said beveled edge of said tubular member cooperating with said chamfered edge of said sheath to facilitate the insertion of said tubular member into said first passageway of said sheath.

7. A bone anchor according to claim 6, wherein said sheath has an inner wall surface, an outer wall surface, and a plurality of ribs protruding radially outwardly from said outer wall surface.

8. A bone anchor according to claim 7, wherein said ribs have bone-engaging edges.

9. A bone anchor according to claim 8, wherein said ribs extend circumferentially about said outer wall surface of said sheath.

10. A bone anchor according to claim 8, wherein said ribs are arranged in a helical fashion on said outer wall surface of said sheath.

11. A bone anchor according to claim 7, wherein said sheath includes at least one axially extending slot which passes completely through said sheath from said outer wall surface thereof to said inner wall surface thereof.

12. A bone anchor according to claim 11, wherein said at least one slot includes a single slot which extends in an axial direction from said proximal end of said sheath to said distal end thereof.

13. A bone anchor according to claim 11, wherein said at least one slot includes a first slot which extends from said proximal end of said sheath toward said distal end thereof and a second slot which extends from said distal end of said sheath toward said proximal end thereof.

14. A bone anchor according to claim 11, wherein said sheath includes at least one hinge formed in said outer wall surface of said sheath.

15. A bone anchor according to claim 11, wherein said sheath includes at least one hinge formed in said inner wall surface of said sheath.

16. A bone anchor according to claim 2, wherein said tubular member includes a generally U-shaped notch which is sized and shaped to accommodate a cable member attached to said washer and passing through said first, second and third passageways.

17. A bone anchor according to claim 1, wherein said washer is separate and independent of said sheath.

18. A bone anchor according to claim 1, wherein said washer is connected to said sheath by a tab which is sized and located so as not to significantly interfere with the radial expansion of said sheath.

19. A bone anchor according to claim 1, wherein at least a portion of said bone anchor is made from a biocompatible polymer which includes a therapeutic agent.

20. A bone anchor, comprising, in combination, a radially expandable sheath having a first passageway which extends axially through said sheath from a proximal end thereof to a distal end thereof; a washer having a second passageway which extends axially through said washer from a proximal end thereof to a distal end thereof, said proximal end of said washer being positionable in abutment with said distal end of said sheath such that said first and second passageways are substantially aligned, said sheath and said washer being sized and shaped such that no portion of said sheath extends into said second passageway of said washer when said sheath is in abutment with said washer; expanding means for radially expanding said sheath without expanding said washer, said expanding means including a tubular member inserted within said first passageway of said sheath from said proximal end thereof toward said distal end thereof, said tubular member having a third passageway extending from a proximal end of said tubular member to a distal end thereof such that said third passageway is arranged substantially coaxially relative to said first and second passageways; and a cable member attached to said washer and passing through said first, second and third passageways to form said combination.

21. A bone anchor, comprising a radially expandable sheath having a first passageway which extends axially through said sheath from one end thereof to an opposite end thereof, a chamfered edge at said one end thereof, an inner wall surface, an outer wall surface, a plurality of ribs protruding radially outwardly from said outer wall surface, at least one axially extending slot which passes completely through said outer wall surface to said inner wall surface, and at least one hinge formed in said outer wall surface, said sheath having an inner diameter which, prior to the radial expansion of said sheath, is determined by the size of said first passageway; a washer having a second passageway which extends axially through said washer from one end thereof to an opposite end thereof, said one end of said washer being positionable adjacent to said opposite end of said sheath such that said first and second passageways are substantially aligned; and expanding means for expanding said sheath in a radial direction, said expanding means including a tubular member having a third passageway extending from one end of said tubular member to an opposite end thereof, and a beveled edge at said opposite end of said tubular member, said tubular member having an outer diameter which is greater than said inner diameter of said sheath prior to the radial expansion of said sheath, said inner diameter of said sheath and said outer diameter of said tubular member are selected so as to create an interference fit between said sheath and said tubular member, said tubular member being insertable into said first passageway of said sheath from said one end thereof toward said opposite end thereof such that said third passageway is arranged substantially coaxially relative to said first and second passageways, said inner diameter of said sheath being increased in response to the insertion of said tubular member into said first passageway of said sheath, said beveled edge of said tubular member cooperating with said chamfered edge of said sheath to facilitate the insertion of said tubular member into said first passageway of said sheath whereby a cable member can be passed through said first, second and third passageways and attached to said washer.

22. A bone anchor, comprising a radially expandable sheath having a first passageway which extends axially through said sheath from one end thereof to an opposite end thereof, a chamfered edge at said one end thereof, an inner wall surface, an outer wall surface, a plurality of ribs protruding radially outwardly from said outer wall surface, at least one axially extending slot which passes completely through said outer wall surface to said inner wall surface, and at least one hinge formed in said inner wall surface, said sheath having an inner diameter which, prior to the radial expansion of said sheath, is determined by the size of said first passageway; a washer having a second passageway which extends axially through said washer from one end thereof to an opposite end thereof, said one end of said washer being positionable adjacent to said opposite end of said sheath such that said first and second passageways are substantially aligned; and expanding means for expanding said sheath in a radial direction, said expanding means including a tubular member having a third passageway extending from one end of said tubular member to an opposite end thereof, and a beveled edge at said opposite end of said tubular member, said tubular member having an outer diameter which is greater than said inner diameter of said sheath prior to the radial expansion of said sheath, said inner diameter of said sheath and said outer diameter of said tubular member are selected so as to create an interference fit between said sheath and said tubular member, said tubular member being insertable into said first passageway of said sheath from said one end thereof toward said opposite end thereof such that said third passageway is arranged substantially coaxially relative to said first and second passageways, said inner diameter of said sheath being increased in response to the insertion of said tubular member into said first passageway of said sheath, said beveled edge of said tubular member cooperating with said chamfered edge of said sheath to facilitate the insertion of said tubular member into said first passageway of said sheath whereby a cable member can be passed through said first, second and third passageways and attached to said washer.

23. A bone anchor, comprising a radially expandable sheath having a first passageway which extends axially through said sheath from one end thereof to an opposite end thereof; a washer having a second passageway which extends axially through said washer from one end thereof to an opposite end thereof, said one end of said washer being positionable adjacent to said opposite end of said sheath such that said first and second passageways are substantially aligned; and expanding means for expanding said sheath in a radial direction, said expanding means includes a tubular member having a third passageway extending from one end of said tubular member to an opposite end thereof and a generally U-shaped notch, said tubular member being insertable into said first passageway of said sheath from said one end thereof toward said opposite end thereof such that said third passageway is arranged substantially coaxially relative to said first and second passageways, whereby a cable member can be passed through said first, second and third passageways and attached to said washer, said U-shaped notch of said tubular member being sized and shaped to accommodate the cable member.

24. A bone anchor, comprising a radially expandable sheath having a first passageway which extends axially through said sheath from one end thereof to an opposite end thereof; a washer having a second passageway which extends axially through said washer from one end thereof to an opposite end thereof, said one end of said washer being positionable adjacent to said opposite end of said sheath such that said first and second passageways are substantially aligned, said washer being connected to said sheath by a tab which is sized and located so as not to significantly interfere with the radial expansion of said sheath; and expanding means for expanding said sheath in a radial direction.

* * * * *